(12) United States Patent
Bayless et al.

(10) Patent No.: US 8,703,478 B2
(45) Date of Patent: Apr. 22, 2014

(54) FLOW-CONTROLLING HEADER

(75) Inventors: David J. Bayless, Athens, OH (US);
Morgan LeFay Vis-Chiasson, Athens, OH (US); Gregory G. Kremer, Athens, OH (US); Ben Stuart, Athens, OH (US)

(73) Assignee: Ohio University, Athens, OH (US)

( * ) Notice: Subject to any disclaimer, the term of this patent is extended or adjusted under 35 U.S.C. 154(b) by 1166 days.

(21) Appl. No.: 12/599,722

(22) PCT Filed: May 19, 2008

(86) PCT No.: PCT/US2008/064067
§ 371 (c)(1),
(2), (4) Date: Nov. 11, 2009

(87) PCT Pub. No.: WO2008/144619
PCT Pub. Date: Nov. 27, 2008

(65) Prior Publication Data
US 2010/0248330 A1    Sep. 30, 2010

Related U.S. Application Data

(60) Provisional application No. 60/938,517, filed on May 17, 2007.

(51) Int. Cl.
*C12M 1/00*    (2006.01)
(52) U.S. Cl.
USPC .................................... 435/292.1; 435/308.1

(58) Field of Classification Search
USPC .............................................. 435/292.1, 308.1
See application file for complete search history.

(56) References Cited

U.S. PATENT DOCUMENTS

| | | | | |
|---|---|---|---|---|
| 4,220,725 | A * | 9/1980 | Knazek et al. | 435/297.4 |
| 6,209,855 | B1 | 4/2001 | Glassford | |
| 7,537,200 | B2 | 5/2009 | Glassford | |
| 2006/0003436 | A1 * | 1/2006 | DiMilla et al. | 435/284.1 |

* cited by examiner

*Primary Examiner* — Jonathan Hurst
(74) *Attorney, Agent, or Firm* — Jason H. Foster; Kremblas & Foster (57) ABSTRACT

An apparatus and method for holding a membrane, screen or other flexible planar body in tension, while providing a conduit for water or other liquid to flow to the membrane being held. The membrane extends from inside a manifold body that carries the liquid, and the manifold body supports the membrane at one edge while the membrane is pulled in tension. Liquid pressure builds up inside the manifold body, preferably by entering a pressure chamber at the top of the manifold body. At a feeding pressure in the pressure chamber the liquid is distributed to the membrane for microbe growth. The liquid can be elevated to a higher, microbe-harvesting pressure by increasing the pressure in the pressure chamber, thereby deflecting a shim separating the pressure chamber from the membrane. The change in pressure is carried out by manually or automatically opening and closing a conventional water valve.

13 Claims, 9 Drawing Sheets

FLOW-CONTROLLING HEADER

BACKGROUND OF THE INVENTION

This invention relates to an apparatus that allows the growth of microbes on a membrane for the purpose of carbon sequestration and/or the growth of biomass fuel.

DESCRIPTION OF THE RELATED ART

It is known that carbon can be sequestered in photosynthetic microbes, as described in U.S. Pat. No. 6,667,171 to Bayless et al., which is incorporated herein by reference. Such microbes can be used for biomass if sequestration is less important than the provision of fuel.

The above-incorporated patent describes an apparatus for growing such photosynthetic microbes in a smaller area than conventional ponds. Although such apparatuses are significant improvements over the conventional technology, problems exist because the membrane upon which the microbes are placed for exposure to the moisture, nutrients and light necessary for survival and growth must be held tightly between at least two points. Additionally, the membrane must permit the flow of the moisture and nutrients onto the microbes, and therefore must be held tightly and consistently across the membrane's length and width.

Therefore, the need exists for an apparatus for holding the membrane edges that also provides nutrients.

BRIEF SUMMARY OF THE INVENTION

A header described and shown evenly applies liquid to a vertically suspended membrane, or a membrane that has a substantial vertical component. The header preferably delivers water and/or an algal/microbe slurry to the membrane in a manner that permits the algae/microbes to be spread evenly over the membrane. The water or other nutrient solution is also delivered evenly, for example, as aided by gravity-assisted capillary flow through the interstices between the fibers of the membrane. An additional feature of the header is to allow for low-impact harvesting by increasing the flow of water over the suspended membrane, which is accomplished in a preferred embodiment by a shim that operates to permit the liquid to flow past at one flow rate, and is flexed under higher pressure to greatly increase the volumetric flow onto the membrane.

An outer pipe has a central channel in which the shim is mounted so that it can flex under pressure to allow greater volume flow. An elongated support body is mounted inside the pipe and the membrane is wrapped around or otherwise attached to the support body. Supporting side plates support the shim at spaced locations, and thereby permit water to flow around the shim. The shim gives good flow control to the water due to the spring characteristics of the shim material. The header has low flow at low pressure when the shim is seated against the pipe wall, and high flow at higher pressure, when the shim is bent away from the wall of the outer pipe under the force of the water's pressure.

The preferred embodiment of the present invention is a mechanism for holding a membrane, screen or other flexible planar body in tension, while also providing a conduit for water or other liquid or slurry to flow to the membrane being held. The membrane extends from inside the header that carries the liquid, and the header supports the membrane at one edge while the membrane is pulled in tension. The preferred embodiment allows liquid pressure to build up inside the header, preferably by entering a pressure chamber at the top of the manifold body, and at a feeding pressure in the pressure chamber the liquid can be elevated to a higher, microbe-harvesting pressure by simply increasing the pressure in the pressure chamber.

In describing the preferred embodiment of the invention which is illustrated in the drawings, specific terminology will be resorted to for the sake of clarity. However, it is not intended that the invention be limited to the specific term so selected and it is to be understood that each specific term includes all technical equivalents which operate in a similar manner to accomplish a similar purpose. For example, the word connected or term similar thereto are often used. They are not limited to direct connection, but include connection through other elements where such connection is recognized as being equivalent by those skilled in the art.

DETAILED DESCRIPTION OF THE INVENTION

Figure 1:
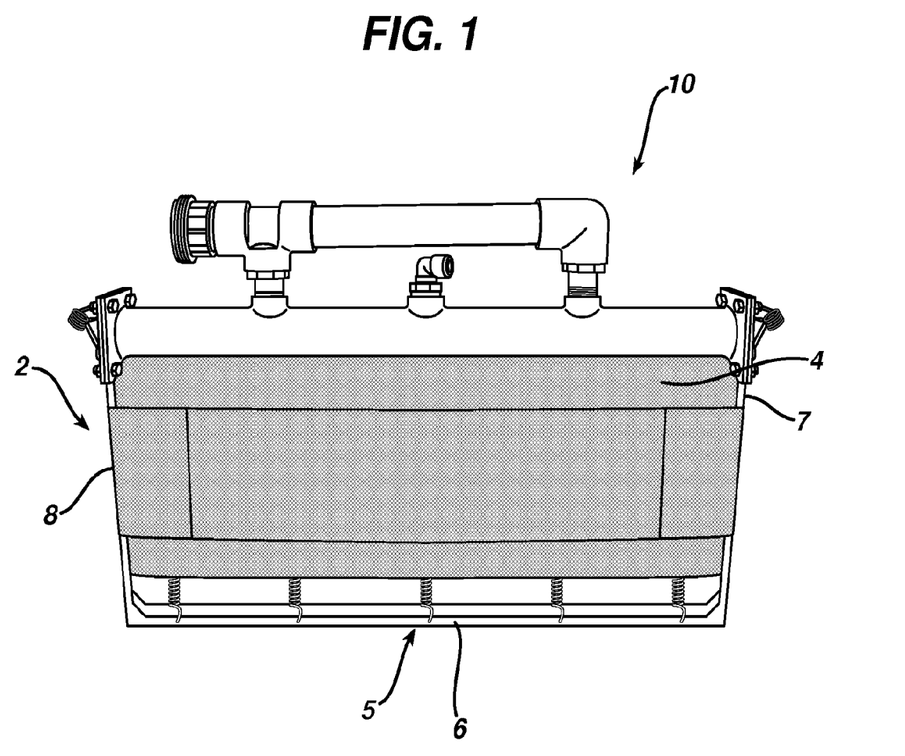
FIG. 1 is a view in perspective illustrating a preferred embodiment of the present flow-controlling header incorporated into an experimental apparatus.

FIG. 1 shows an embodiment of the invention in cooperation with other parts of a membrane-holding apparatus 2. A membrane 4 is mounted to a lower membrane support 5 and a header 10. The lower membrane support 5 has a first member 6 that is substantially parallel to the header 10, and lateral members 7 and 8 that extend between the first member 6 and the header 10. The first member 6 receives one edge of the membrane 4, such as the edge that is opposite the edge supported by the header 10, and the lateral members 7 and 8 receive opposing lateral edges of the membrane 4. One manner of the members 6, 7 and 8 receiving the membrane edges is by being inserted in looped edges of the membrane. It should be noted that the lower membrane support 5 and its mechanism for receiving the membrane 4, can be replaced by various other structures for supporting at least an edge of the membrane 4.

Figure 8:
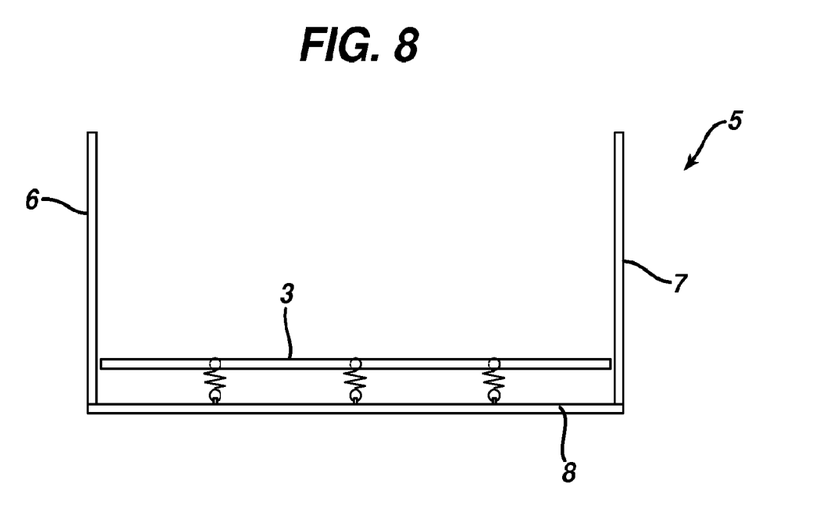
FIG. 8 is a side view illustrating a lower membrane support shown in FIG. 1.

The apparatus shown in FIG. 1 shows one example of such a lower membrane support, which, in the alternatives contemplated, holds the edge or edges of the membrane opposite the header 10. In a preferred embodiment, the moveable member 3 (shown in FIG. 8) of the lower membrane support 5 exerts a tensile force on the edge of the membrane 4, thereby causing the membrane 4 to be drawn tightly between the header 10 and the first member 6, and between the lateral members 7 and 8. Other tensioning structures are contemplated, and are not critical to the present invention.

Figure 2:
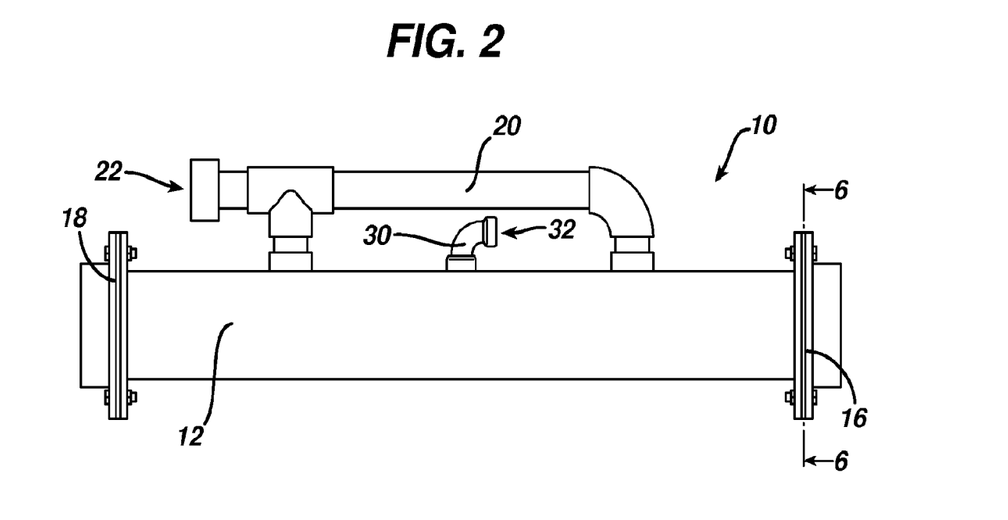
FIG. 2 is a side schematic view of the flow-controlling header of the embodiment of FIG. 1.
Figure 3:
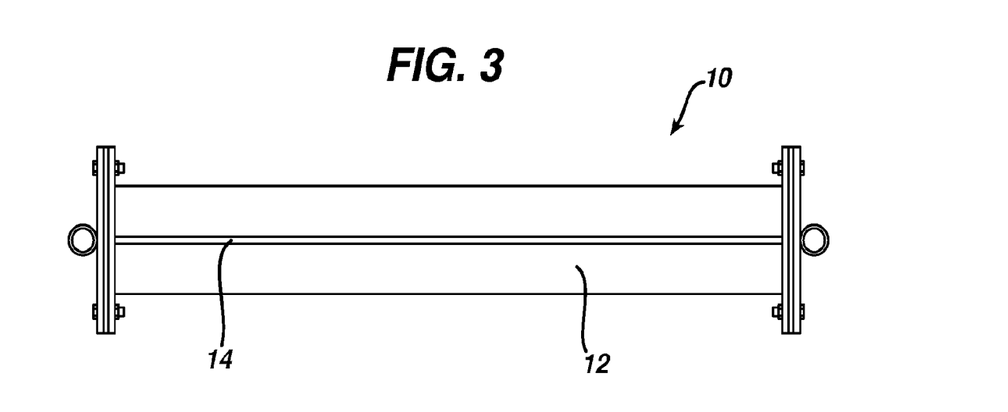
FIG. 3 is a bottom schematic view of the flow-controlling header of the embodiment of FIG. 1.
Figure 4:
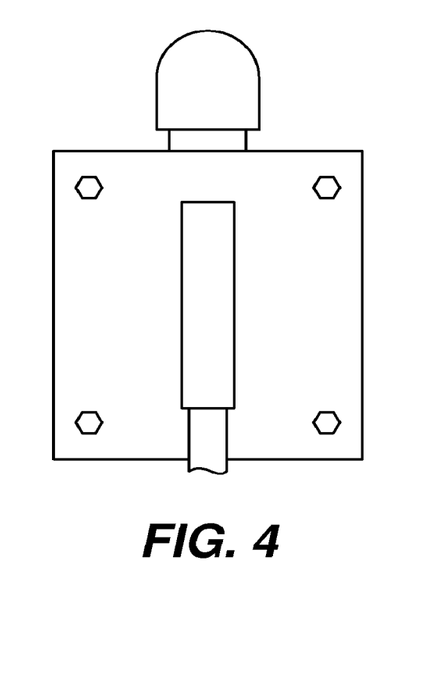
FIG. 4 is an end schematic view of the flow-controlling header illustrated in FIG. 2.
Figure 5:
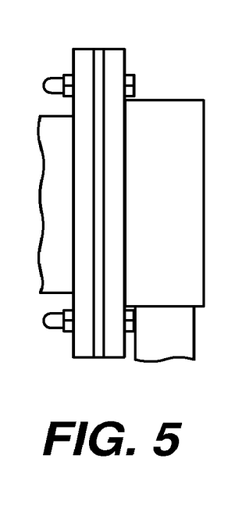
FIG. 5 is side schematic view of an end portion of the flow-controlling header illustrated in FIG. 2.

In FIGS. 2 and 3, the header 10 is shown in greater detail. The header 10 has a manifold body 12, which is preferably made from a conventional water pipe having a diameter in the range of 4 to 6 cm. The body 12 is hollow, and is most preferably made from a conventional pipe material, such as polyvinyl chloride (PVC), acrylonitrile butadiene styrene (ABS), stainless steel, aluminum or fiberglass composite. Of course, other materials will become apparent to persons of ordinary skill from the description herein, and therefore the body 12 can be any hollow body that is cast or otherwise molded or manufactured to form a manifold that functions equivalently to the manifold bodies shown and described herein.

The body 12 has ends 16 and 18 that seal the main chamber 17 within the body 12 from the exterior of the body 12, and provide a mounting point for the entire apparatus 2. The ends 16 and 18 are preferably made of flanges rigidly mounted to the body 12, such as by welding or adhesive, to which similarly shaped plates are mounted with removable fasteners, such as screws. A gasket is preferably mounted therebetween to seal the abutting surfaces. Such a structure closes the ends of the body and permits the attachment of multiple similar bodies to one another longitudinally, thereby allowing one to make a header of any desired length. Alternatively, the body 12 can be manufactured to any desired length, such as by extrusion, pultrusion or casting. In the embodiment of FIG. 1, the body 12 is approximately one meter long. The membrane is approximately the same length and approximately 30 cm tall, although this is an experimental apparatus used for a limited purpose. Contemplated operational apparatuses are in the range of a few meters tall and many meters long.

A first conduit 20, which is preferably made of conventional water pipe, is mounted to the body 12 with its inner passage (not visible) in fluid communication with the chamber within the body 12. Therefore, any fluent material that is forced into the conduit 20 through the inlet 22 passes therethrough into the chamber of the body 12, and vice versa. Preferably a centrifugal pump is in fluid communication with the conduit 20, and pumps a nutrient liquid, such as water containing nutrients necessary and/or desirable for the survival and growth of the microbes on the membrane, into the chamber of the body 12.

A second conduit 30, which is preferably made of conventional water pipe, is mounted to the body 12 with its inner passage (not visible) in fluid communication with the chamber within the body 12. Therefore, any fluent material that is forced into the conduit 30 through the inlet 32 passes therethrough into the chamber of the body 12, and vice versa. A positive displacement pump, such as a diaphragm pump, is in fluid communication with the conduit 30, and pumps a liquid containing microbes into the chamber of the body 12 when it is desirable to inoculate the membrane with microbes.

Figure 6:
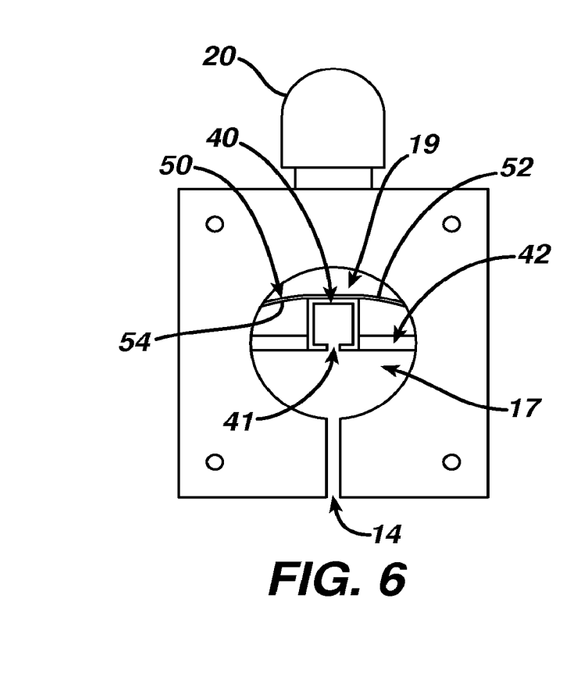
FIG. 6 is an end view through the line 6-6 of FIG. 2.

The body 12 has an elongated opening, such as the slot 14, preferably extending the entire length of the body 12, but it is contemplated that the slot can be only a portion of the body's length. The slot 14 permits the membrane 4 to extend from attachment to a membrane support within the body 12 to the lower membrane support 5 outside the body 12. As shown in FIG. 6, the slot 14 is formed at the lower end of the chamber 17 within the body 12, and extends through a portion of the ends 16 and 18. The slot 14 is preferably formed in the region of the body 12 that will be oriented in the downward direction when the header 10 is mounted in an operable orientation, and is substantially opposite to the first and second conduits 20 and 30 where liquid enters the chamber 17.

Figure 10:
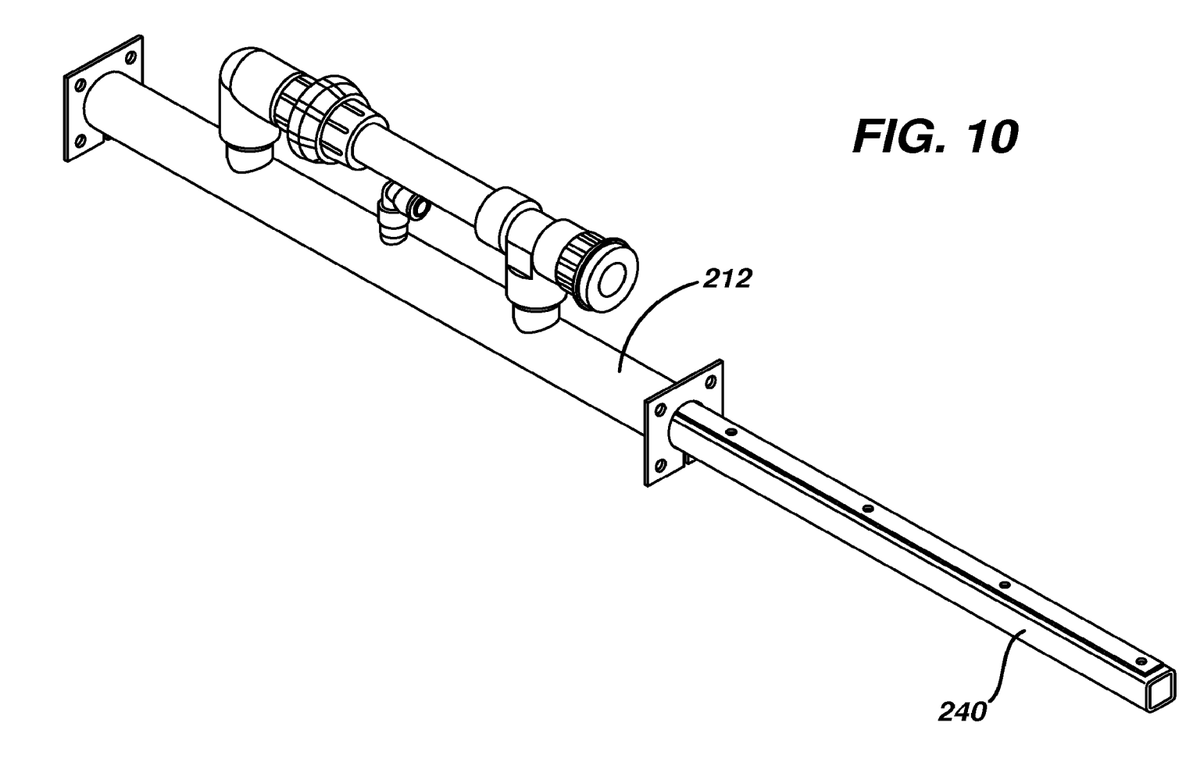
FIG. 10 is a view in perspective illustrating another alternative embodiment of the flow-controlling header of the present invention.
Figure 11:
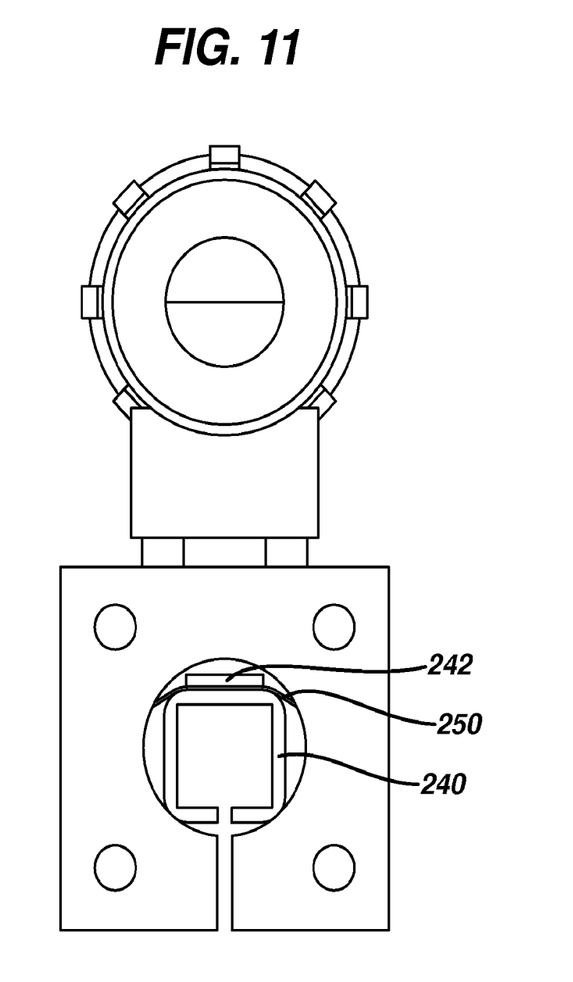
FIG. 11 is an end view illustrating the embodiment of FIG. 10.
Figure 12:
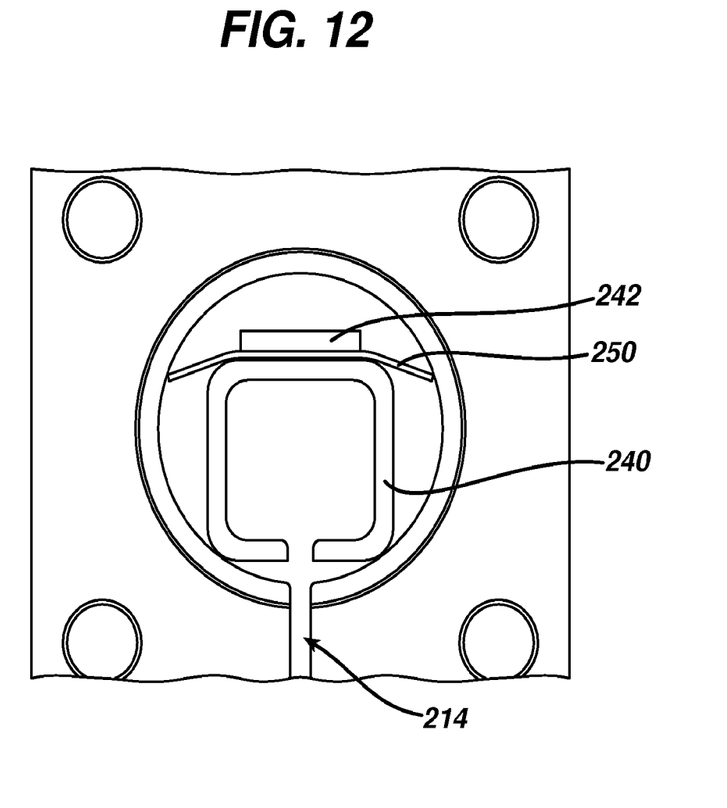
FIG. 12 is an end view illustrating the embodiment of FIG. 10.
Figure 13:
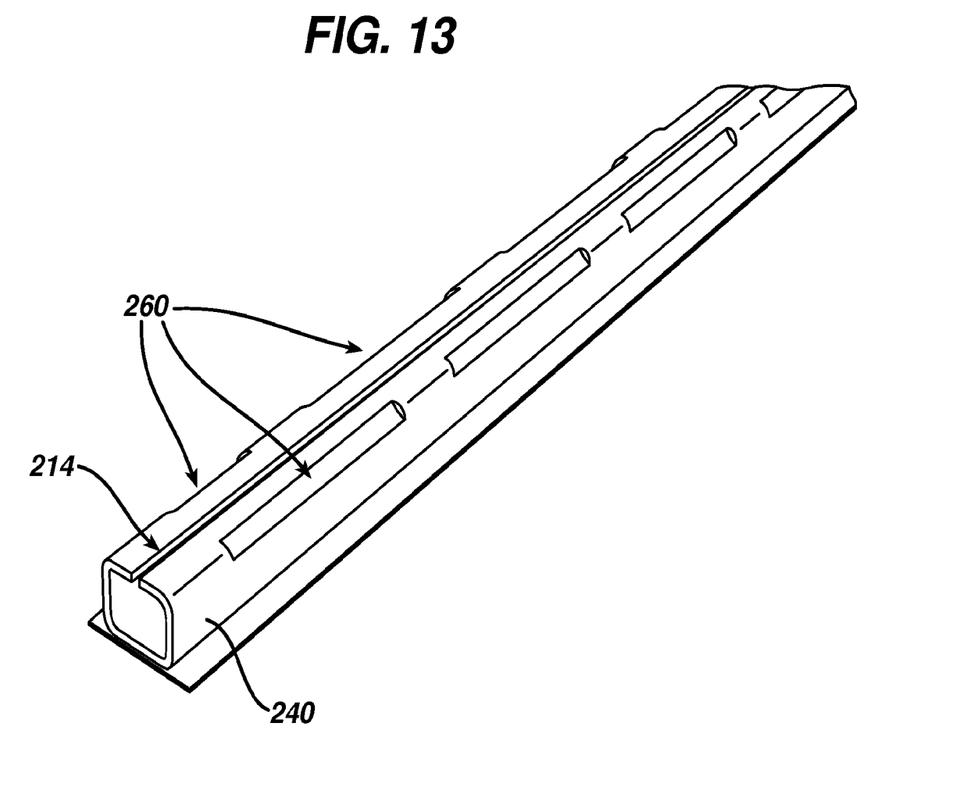
FIG. 13 is a view in perspective illustrating a membrane support and shim of the embodiment of FIG. 10.

The membrane support 40, which is a C-shaped, rigid support member that holds the membrane 4, is mounted within the chamber 17. The membrane extends around one or more hollow or solid rods (not shown) having a total width that, when combined with the membrane, is at least a substantial amount larger than the width of the opening 41 at the lower end of the support 40. The rod and membrane edge are inserted into the opening in the support 40 and extended longitudinally into the body 12, as shown in FIG. 10 for a different embodiment of the invention. When thus installed, the rod and membrane combination cannot be pulled through the opening 41, and the membrane support 40 thereby provides support against removal of the rod and membrane from the body 12. This permits a tensile force to be applied to the end of the membrane 4 that is opposite the header 10 as described herein.

The support 40 is preferably made of a plurality of discrete C-channel pieces mounted along the length of the body 12 to the web 42, such as by welding or adhesive. The web 42 is preferably a flat body, such as plate, that is mounted at its outermost edges to the inwardly facing wall of the body 12, such as by welding or adhesive. There are preferably large gaps between the ends of such discrete C-channel pieces, thereby allowing water in the chamber 17 to flow freely between opposite sides of the web 42. Thus, the web 42 rigidly mounts the support 40 to the body 12 so that a force applied to the membrane is supported by the support 40, and is carried through the web 42 to the body 12.

A shim 50 extends from one side of the inner wall of the body 12 to another side, preferably extending along a chord of the preferably circular inner wall of the body 12, and toward the ends 16 and 18. The shim 50 mounts to the support 40, such as by gluing or clamping, and its legs 52 and 54 extend as cantilevers from the support 40 to the inner wall of the body 12.

Figure 7:
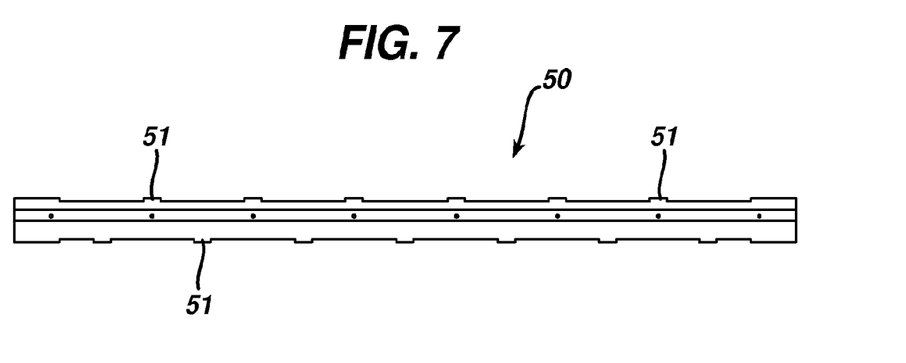
FIG. 7 is a top view illustrating a shim that is used in an embodiment of the present invention.

In a preferred embodiment of the invention, the shim 50 is rectangular, except that small portions of the shim edges are removed, as shown in FIG. 7, to create tabs 51 separated by gaps. Referring to FIG. 6, the legs 52 and 54 define the pressure chamber 19, which is a subsection within the main chamber 17 of the body 12. The legs 52 and 54 form a seal, more or less, at the points where the legs 52 and 54 contact the inner wall of the body 12. More preferably, the contact between the legs 52 and 54 is discontinuous, such as only at the tabs 51, thereby permitting liquid to flow through the gaps between the tabs 51, and thus between the pressure chamber 19 and the remaining portion of the chamber 17. Of course, shapes are contemplated other than the gaps illustrated to accomplish the flow of liquid described, including a saw tooth shape, a scalloped shape, roughened edges or any other surface or material at the edges of the legs 52 and 54 that permits some liquid flow past the shim 50.

The shim 50 is made of a flexible material having a spring constant sufficient to cause the legs 52 and 54 to spring back to their slightly bent shape from deflection caused by pressurized water in the pressure chamber 19. For example, the shim 50 can be a sheet of polyethylene, PVC or any plastic, composite or other material that provides sufficient spring constant and durability. When bent and released, the legs 52 and 54 return to the substantially planar configuration shown in FIG. 6 due to this spring constant. The shim can be varied in shape or spring constant to obtain the results desired.

The preferred shim material is a thin sheet, and is preferably planar, but can be any shape that permits the formation of a pressure chamber at the opposite side of the shim as the slot 14. Likewise, other attachment configurations are contemplated, such as attachment at one shim edge to the manifold body sidewall or the membrane support, and extending as a single cantilever to the other. It is also contemplated that fluid can be routed through the manifold body from a fluid inlet on one side of the body to the slot at the other side. In such an embodiment, the shim 50 is intermediate the slot and the inlet by being intermediate the flow path of the fluid, even if it is not located on a line connecting the inlet and the slot.

The shim 50 is positioned in the chamber 17 to create the pressure chamber 19 at about one-eighth of the cross sectional area of the chamber 17, thereby giving the pressure chamber 19 a small volume to fill up. Of course, this fraction can be greater or less than one-eighth. The pressure can thus be distributed along the entire length of the manifold body 12, and the shim 50 provides resistance to flow from the pressure chamber 19 past the shim 50. When the pressure increases sufficiently to deflect the shim's legs 52 and 54 away from the manifold body 12 sidewall, a small amount of pressure change will cause the shim 50 to deflect away from the body 12 sidewall and allow substantially more water to flow between the shim 50 and the body 12 sidewall.

Any liquid that flows into the pressure chamber 19 and past the legs 52 and 54 flows toward the slot 14 due to the force of gravity and the configuration of the slot 14 on the lowest part of the body 12. The liquid then flows onto the membrane passing out of the slot 14, and preferably continues, by sheeting action and by flowing through the interstices of the fibers of the membrane, as well as through the fibers themselves if they are liquid-permeable, downwardly toward the lower membrane support 5. As the liquid flows along and within the membrane 4, it provides the necessary moisture and nutrients to the microbes that are on the membrane 4.

In summary, therefore, when water or any other fluent material is forced through the conduit 20 into the pressure chamber 19, the pressure chamber 19 is pressurized, and the shim 50 permits a low rate of water to flow past the legs 52 and 54. As noted above, the shim 50 is designed to bend substantially upon the application of sufficient force. Thus, when a greater pressure is built up in the liquid in the pressure chamber 19, the legs 52 and 54 of the shim 50 are forced by this pressure to deflect away from the inner wall of the body 12, thereby permitting substantially more liquid to flow past the legs 52 and 54 at the higher flow rate.

It should be noted that there are at least two flow rates: (1) a lower flow rate at which liquid flows into the pressure chamber 19 and flows past the shim 50 onto the membrane 4, and (2) a significantly higher flow rate when the pressure of liquid in the pressure chamber 19 is raised sufficiently, thereby causing the legs 52 and 54 to separate from the inner wall of the body 12. This separation permits substantially higher volumetric flow rate of liquid onto the membrane. The first flow rate is referred to herein as the "growth" or "feeding" flow rate, because it is at this flow rate that the liquid is applied to the membrane to feed the microbes to cause them to grow. The second flow rate is referred to herein as the "harvesting" flow rate, because this is the rate at which microbes are physically removed from the membrane for other uses, such as biomass fuel.

It is also possible for a third, intermediate flow rate, which is about twice the feeding flow rate, and which is used to inoculate a new membrane with microbes, such as cyanobacteria. The lower flow rate for "feeding" the microbes is too slow to use when adding microbes, which is referred to as "inoculation", to the membrane through the conduit 30. Therefore, an intermediate flow rate that is higher than the "feeding" flow rate is desired for when one first adds bacteria to the membrane.

To gain additional information, a comparative test was performed. In the first test, a drilled-hole header without a shim was used. Approximately 0.6 gallons per minute (gpm) flow rate was maintained during growth mode to grow the microbes. The microbes grew well on the membrane, and showed the qualities of adhering to the membrane. At the end of a five-week test an attempt was made to harvest the organisms from the membrane by increasing the flow rate above the feeding rate. The attempt at harvesting did not produce the desired results. The membrane material was Omnisil, which is a woven cloth made up of continuous filament amorphous silica. Alternative materials can, of course, be used.

In a second test, the shimmed header according to the invention was used. The feeding rate was a success and the organisms adhered well to the membrane. Flow rates of approximately 0.5 gpm were used. Shims tested were of thicknesses of 0.015 inch, 0.020 inch and 0.025 inch. This design showed good flow characteristics and there was no appreciable clogging. After several weeks, sufficient growth was established on the membranes. A harvesting test was then performed by increasing the flow rate. It was not possible to dislodge a substantial amount of organisms from the membrane using a flow rate of approximately 2 gpm, which did not produce a full "sheeting action" desired for harvesting.

To test if harvesting could be achieved using this type of header design modified to allow higher harvesting flow rates, a "sheeting action" flow was simulated on the FIG. 1 embodiment without an impingement jet by removing the first conduit 20 from the header 10 and using the full flow rate of the centrifugal pump on a portion of the membrane 4. This enabled the dislodgement of an appreciable amount of the microbes from the "harvested" section of the membrane. The flow rate was 1.55 gpm, and it was directed to the left ⅓ of the membrane.

The results of this test indicated that harvesting is possible using only high-flow sheeting action without an impingement jet. The tests performed also showed that organisms re-grow on the "cleaned" section of a membrane after harvesting. Thus, continuous bioreactor operation is feasible with continuous cycles of harvesting and repopulating membranes. It is estimated that 5-10 gallons per minute is needed to achieve the desired level of harvesting for the entire membrane. The flow to the header 10 through the conduit 20 has a flow capacity of at least 10 to 20 gpm while still maintaining a low flow capacity for growth/feeding mode. The conduit 20 can readily deliver over 20 gpm of flow with modifications apparent to the person of ordinary skill. The change in pressure preferably is carried out by manually or automatically opening and closing a conventional water valve. Of course, the pressure can be changed by other mechanisms, such as variable pressure pumps, turning on and off single pumps in an arrangement of a plurality of pumps, varying the opening sizes of the inlet conduit, etc.

Figure 9:
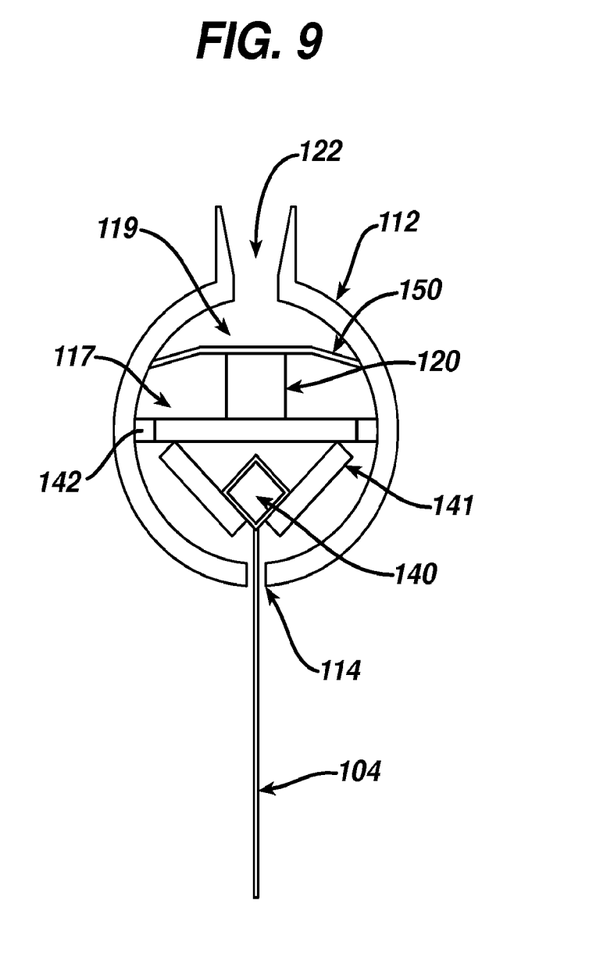
FIG. 9 is an end view illustrating an alternative embodiment of the flow-controlling header of the present invention.

An alternative embodiment of the invention is shown in FIG. 9, in which a manifold body 112 has an internal chamber 117 and a web 142 extending between the walls of the body 112. A support, preferably the box-beam 140, extends within a V-shaped member 141 mounted to the web 142, and the membrane 104 extends around the box-beam 140 through the slot 114. A beam 120 is mounted to the side of the web 142 opposite the slot 114, and the shim 150 is mounted to the top of the beam 120 with legs that extend to the wall of the body 112. Thus, the pressure chamber 119 defined between the shim 150, the body walls 112 and the inlet 122 is on the top of the body 112 substantially on the opposite side of the shim 150 as the slot 114.

Yet another embodiment of the invention is shown in FIGS. 10 through 13, in which the manifold body 212 has a support member, such as the beam 240, mounted therein with a shim 250 mounted to the beam 240 by clamping pressure applied by a strip 242 mounted to the beam 240 using screws. The beam 240 has gaps 260 formed on the opposite side from the shim 250, thereby permitting liquid passing the shim 250 to flow past the beam 240 into the slot 214 through which the membrane (not shown) extends.

This detailed description in connection with the drawings is intended principally as a description of the presently preferred embodiments of the invention, and is not intended to represent the only form in which the present invention may be constructed or utilized. The description sets forth the designs, functions, means, and methods of implementing the invention in connection with the illustrated embodiments. It is to be understood, however, that the same or equivalent functions and features may be accomplished by different embodiments that are also intended to be encompassed within the spirit and scope of the invention and that various modifications may be adopted without departing from the invention or scope of the following claims.

The invention claimed is:

1. An apparatus for holding a membrane and supplying fluent material to the membrane, the apparatus comprising:
   (a) a manifold having a manifold sidewall defining a main chamber with an elongated opening in the manifold sidewall;
   (b) a membrane support within the main chamber to which the membrane is configured to attach in tension;
   (c) a fluid inlet formed through the manifold sidewall;
   (d) a shim mounted in the main chamber intermediate the elongated opening and the fluid inlet, the shim extending from the membrane support to the manifold sidewall, thereby defining a pressure chamber on an inlet side of the shim, wherein the shim is configured to deflect when a predetermined fluid pressure is reached in the pressure chamber, thereby permitting fluid to flow past the shim to the membrane.

2. The apparatus in accordance with claim 1, wherein the shim is mounted to the membrane support and extends from contact with one side of the manifold sidewall to contact with another side of the manifold sidewall.

3. The apparatus in accordance with claim 1, wherein the shim extends from attachment to the manifold sidewall to contact with the membrane support.

4. The apparatus in accordance with claim 2, wherein the fluid inlet is formed through the manifold sidewall on a side thereof that is substantially opposite the elongated opening.

5. The apparatus in accordance with claim 4, wherein the membrane support is mounted to the manifold sidewall.

6. The apparatus in accordance with claim 4, wherein the membrane support seats against the manifold sidewall.

7. The apparatus in accordance with claim 4, wherein the elongated opening is a slot that is configured to pass the membrane through.

8. The apparatus in accordance with claim 7, wherein the elongated opening faces a substantially downward direction.

9. A method of holding a membrane and supplying fluent material to the membrane, the method comprising:
   (a) disposing a manifold above a lower membrane support, the manifold having a manifold sidewall defining a main chamber with an elongated opening and a fluid inlet formed through the manifold sidewall;
   (b) disposing an upper membrane support within the main chamber;
   (c) extending the membrane through the elongated opening and attaching the membrane to the upper membrane support;
   (d) applying tension to the membrane;
   (e) mounting a shim in the main chamber intermediate the elongated opening and the fluid inlet and extending from the membrane support to the manifold sidewall, thereby defining a pressure chamber on a fluid inlet side of the shim;
   (f) forcing fluent material through the fluid inlet into the pressure chamber at a first pressure in the pressure chamber to achieve a first flow rate of fluent material onto the membrane and through the elongated opening; and
   (g) increasing the pressure of fluent material in the pressure chamber to a second, higher pressure, thereby deflecting the shim to achieve a second, higher flow rate of fluent material past the shim.

10. The method in accordance with claim 9 wherein the step of attaching the membrane to the upper membrane support further comprises wrapping an edge of the membrane around a beam and inserting the beam in the main chamber.

11. The method in accordance with claim 9 wherein the step of attaching the membrane to the upper membrane support further comprises wrapping an edge of the membrane around a rod and inserting the rod into a beam in the main chamber.

12. An apparatus for holding a membrane and supplying fluent material to the membrane, the apparatus comprising:
   (a) a manifold having a manifold sidewall defining a main chamber with an elongated opening formed through the manifold sidewall whereby the main chamber is in fluid communication with the exterior of the manifold;
   (b) a membrane support mounted within the main chamber and spaced from the manifold sidewall to permit fluid to flow thereby, the membrane support being to which the membrane is configured to attach in tension;
   (c) a fluid inlet formed through the manifold sidewall; and
   (d) a shim mounted in the main chamber intermediate the elongated opening and the fluid inlet, the shim extending from the membrane support to the manifold sidewall, thereby defining a pressure chamber on an inlet side of the shim, wherein the shim is configured to deflect when a predetermined fluid pressure is reached in the pressure chamber, thereby permitting fluid to flow past the shim to the membrane.

13. An apparatus holding a membrane for supplying fluent material to the membrane, the apparatus comprising:
   (a) a manifold having a manifold sidewall defining a main chamber within and an elongated opening formed through the manifold sidewall through which the main chamber is in fluid communication with the exterior of the manifold;
   (b) a membrane support mounted within the main chamber and spaced from the manifold sidewall to form at least one gap between the membrane support and the manifold sidewall through which fluid can flow;
   (c) a membrane mounted to the membrane support in tension;
   (d) a fluid inlet formed through the manifold sidewall; and
   (e) a moveable shim mounted in the main chamber intermediate the elongated opening and the fluid inlet, the shim extending from the membrane support across said at least one gap to the manifold sidewall, thereby defining a pressure chamber within the main chamber on an inlet side of the shim, wherein the shim is configured to deflect when a predetermined fluid pressure is reached in the pressure chamber, thereby permitting fluid to flow past the shim to the membrane.

* * * * *